US012638408B2

(12) United States Patent     (10) Patent No.:   US 12,638,408 B2

Akimoto et al.     (45) Date of Patent:     May 26, 2026

(54) SENSOR AND SENSOR SYSTEM

(71) Applicant: KABUSHIKI KAISHA TOSHIBA, Tokyo (JP)

(72) Inventors: Yosuke Akimoto, Yokohama Kanagawa (JP); Akira Fujimoto, Kawasaki Kanagawa (JP); Yoshihiko Kurui, Chigasaki Kanagawa (JP); Ping Wang, Fujisawa Kanagawa (JP); Hiroaki Yamazaki, Yokohama Kanagawa (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 356 days.

(21) Appl. No.: 18/354,713

(22) Filed: Jul. 19, 2023

(65) Prior Publication Data

US 2024/0295516 A1    Sep. 5, 2024

(30) Foreign Application Priority Data

Mar. 2, 2023   (JP) ................................. 2023-032015

(51) Int. Cl.
    *G01N 27/12*     (2006.01)
    *G01N 33/00*     (2006.01)

(52) U.S. Cl.
    CPC ......... *G01N 27/12* (2013.01); *G01N 33/0027* (2013.01)

(58) Field of Classification Search
    CPC .... G01N 27/12; G01N 27/121; G01N 27/122; G01N 27/123; G01N 27/124; G01N 27/128; G01N 33/0027
    See application file for complete search history.

(56) References Cited

U.S. PATENT DOCUMENTS 5,464,966 A    11/1995   Gaitan et al.
5,659,127 A *   8/1997   Shie ...................... G01N 27/12
                                338/334

(Continued)

FOREIGN PATENT DOCUMENTS

EP      3 534 154 A1    9/2019
JP    2016-156623 A    9/2016

(Continued)

OTHER PUBLICATIONS

Japan Patent Office, Office Action in JP App. No. 2023-032015 (Dec. 24, 2025).

*Primary Examiner* — Paul M. West

(74) *Attorney, Agent, or Firm* — Finnegan, Henderson, Farabow, Garrett & Dunner, LLP

(57) ABSTRACT

According to one embodiment, a sensor includes an element portion including a first base and a first element. The first element includes, a first fixed member fixed to the first base, a first resistance connecting member supported by the first fixed member, a first conductive connecting member supported by the first fixed member, and a first film portion supported by the first resistance connecting member and the first conductive connecting member. A first gap is provided between the first base and the first film portion. The first film portion includes a first resistance layer and a first conductive layer. The first resistance connecting member includes a first resistance wiring electrically connected to the first resistance layer. The first conductive connecting member includes a first conductive wiring electrically connected to the first conductive layer.

20 Claims, 5 Drawing Sheets

(56) References Cited

U.S. PATENT DOCUMENTS

| | | | |
|---|---|---|---|
| 2018/0292338 A1 | 10/2018 | Liu et al. | |
| 2021/0318282 A1 | 10/2021 | Akimoto et al. | |
| 2022/0221416 A1* | 7/2022 | Kimura | G01N 27/128 |
| 2023/0341343 A1* | 10/2023 | Baesler | G01N 1/44 |
| 2024/0201117 A1* | 6/2024 | Shibata | G01N 27/16 |

FOREIGN PATENT DOCUMENTS

| | | | |
|---|---|---|---|
| JP | 2017-36935 A | | 2/2017 |
| JP | 2018-77129 A | | 5/2018 |
| JP | 2019-152451 A | | 9/2019 |
| JP | 2019-158358 A | | 9/2019 |
| JP | 2021-167766 A | | 10/2021 |

* cited by examiner

FIG. 3A
w11F
11F
11r
11b
11c
11i
11a
D1
Z
X
D2
Y
D3
51s
g1
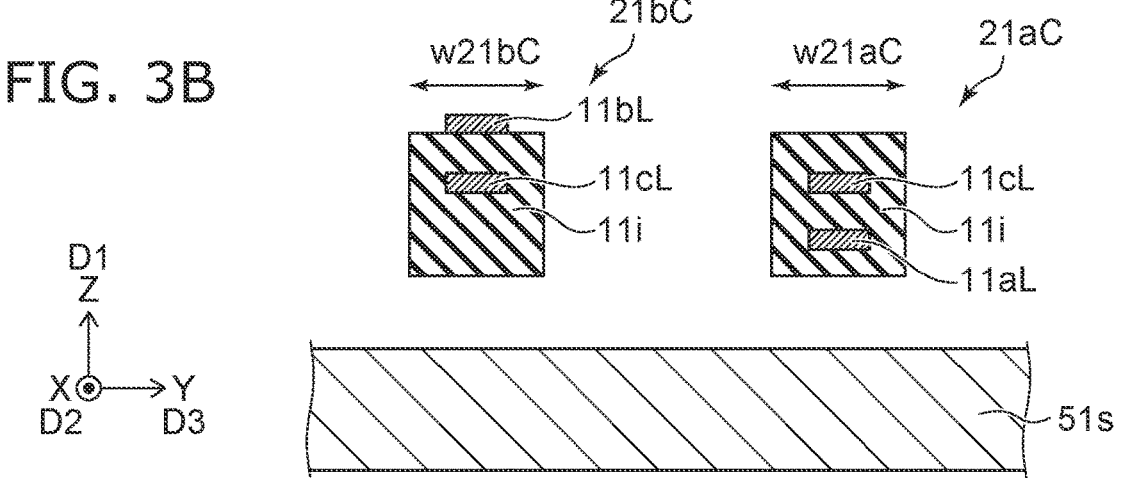
FIG. 3B
21bC
w21bC
21aC
w21aC
11bL
11cL
11i
11cL
11i
11aL
D1
Z
X
D2
Y
D3
51s
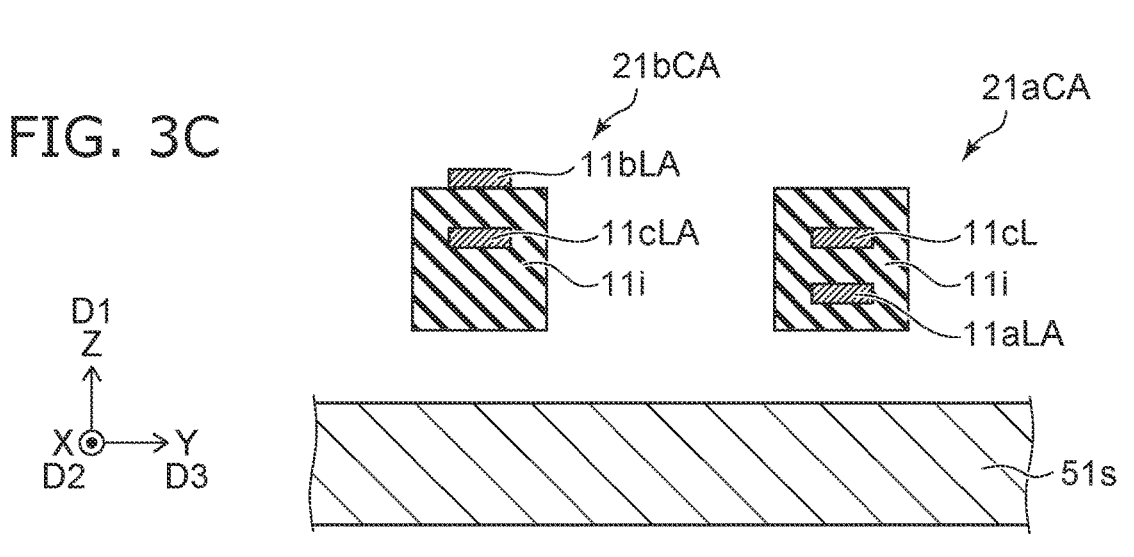
FIG. 3C
21bCA
21aCA
11bLA
11cLA
11i
11cL
11i
11aLA
D1
Z
X
D2
Y
D3
51s

SENSOR AND SENSOR SYSTEM

CROSS-REFERENCE TO RELATED APPLICATIONS

This application is based upon and claims the benefit of priority from Japanese Patent Application No. 2023-032015, filed on Mar. 2, 2023; the entire contents of which are incorporated herein by reference.

FIELD

Embodiments described herein relate generally to a sensor and a sensor system.

BACKGROUND

Embodiments of the present invention provide sensors and sensor systems capable of improving characteristics.

BRIEF DESCRIPTION OF THE DRAWINGS

FIGS. 3A to 3C are schematic cross-sectional views illustrating the sensor according to the first embodiment;

DETAILED DESCRIPTION

Figure 1:
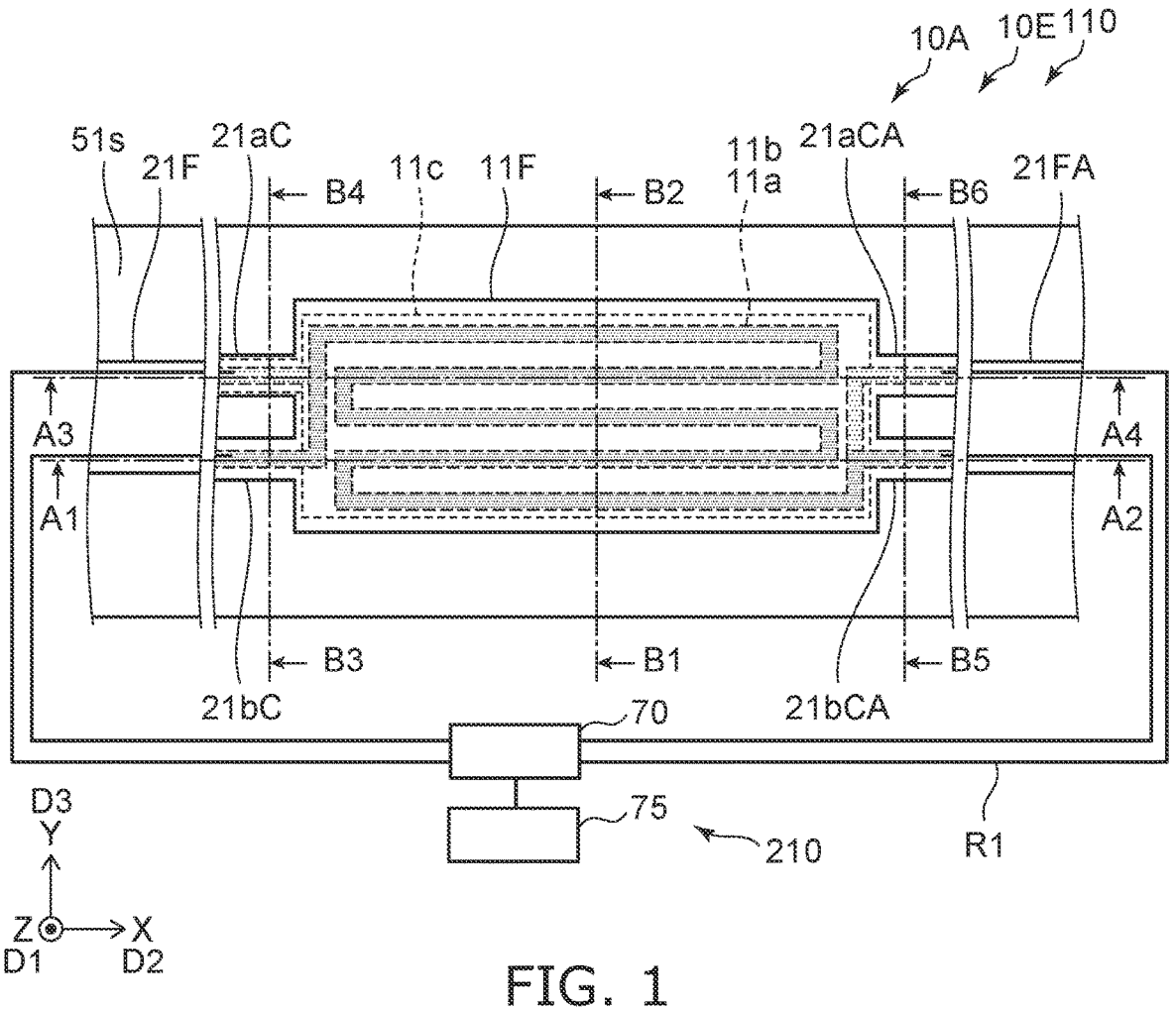
FIG. 1 is a schematic plan view illustrating a sensor according to a first embodiment.

According to one embodiment, a sensor includes an element portion including a first base and a first element. The first element includes, a first fixed member fixed to the first base, a first resistance connecting member supported by the first fixed member, a first conductive connecting member supported by the first fixed member, and a first film portion supported by the first resistance connecting member and the first conductive connecting member. A first gap is provided between the first base and the first film portion. The first film portion includes a first resistance layer and a first conductive layer. The first resistance connecting member includes a first resistance wiring electrically connected to the first resistance layer. The first conductive connecting member includes a first conductive wiring electrically connected to the first conductive layer.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic plan view illustrating a sensor according to a first embodiment.

Figure 2A:
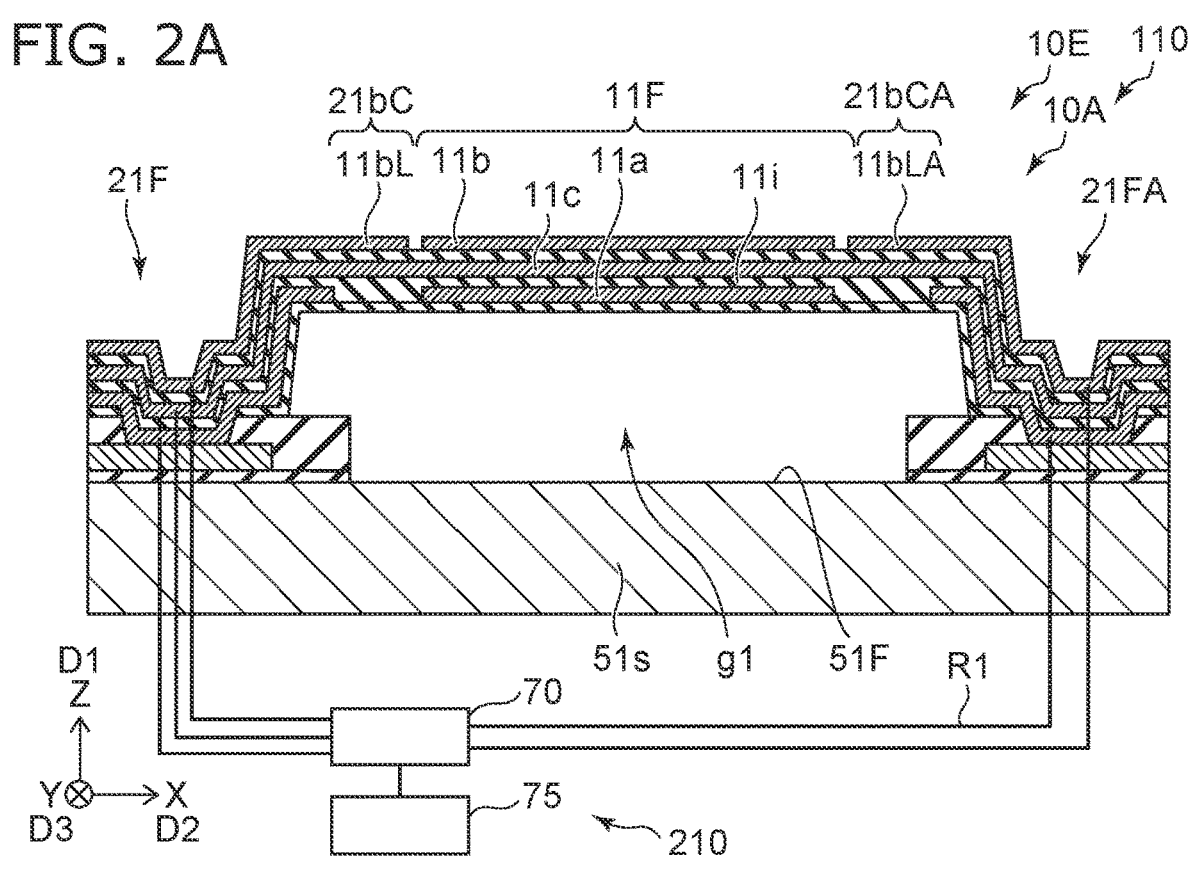
FIGS. 2A and 2B are schematic cross-sectional views illustrating the sensor according to the first embodiment.
Figure 2B:
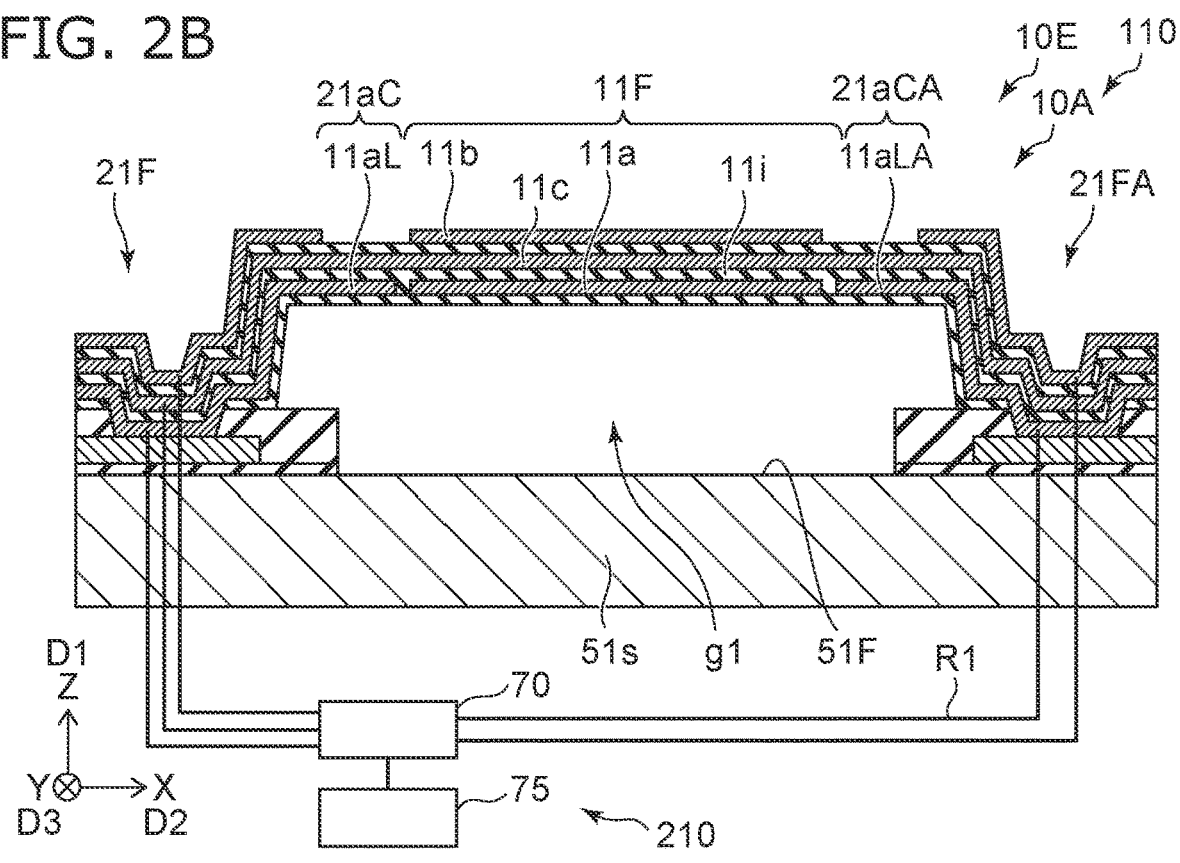

FIGS. 2A and 2B are schematic cross-sectional views illustrating the sensor according to the first embodiment.

FIGS. 3A to 3C are schematic cross-sectional views illustrating the sensor according to the first embodiment.

FIG. 2A is a cross-sectional view taken along the line A1-A2 of FIG. 1. FIG. 2B is a cross-sectional view taken along the line A3-A4 of FIG. 1. FIG. 3A is a cross-sectional view taken along the line B1-B2 of FIG. 1. FIG. 3B is a cross-sectional view along the line B3-B4 of FIG. 1. FIG. 3C is a cross-sectional view taken along the line B5-B6 of FIG. 1.

As shown in FIGS. 1, 2A and 2B, a sensor 110 according to the embodiment includes an element section 10E. The element section 10E includes a first base 51s and a first element 10A.

The first base 51s may include, for example, a silicon substrate. The first base 51s may include electronic circuits such as transistors.

The first element 10A includes a first fixed member 21F fixed to the first base 51 s, a first resistance connecting member 21aC supported by the first fixed member 21F, a first conductive connecting member 21bC supported by the first fixed member 21F, and a first film portion 11F supported by the first resistance connecting member 21aC and the first conductive connecting member 21bC.

A first gap g1 is provided between the first base 51s and the first film portion 11F. A first direction D1 from the first base 51s to the first fixed member 21F is defined as a Z-axis direction. One direction perpendicular to the Z-axis direction is defined as an X-axis direction. A direction perpendicular to the Z-axis direction and the X-axis direction is defined as a Y-axis direction.

The first base 51s includes a first face 51F. The first face 51F extends along the X-Y plane. The first fixed member 21F is fixed to the first face 51F.

The first film portion 11F includes a first resistance layer 11a and a first conductive layer 11b. In this example, the first film portion 11F further includes a first conductive member 11c. The first conductive member 11c will be described below.

As shown in FIGS. 2B and 3B, the first resistance connecting member 21aC includes a first resistance wiring 11aL electrically connected to the first resistance layer 11a. As shown in FIGS. 2A and 3B, the first conductive connecting member 21bC includes a first conductive wiring 11bL electrically connected to the first conductive layer 11b.

For example, the first resistance connecting member 21aC does not include the first conductive wiring 11bL. The first conductive connecting member 21bC does not include the first resistance wiring 11aL. The first conductive wiring 11bL does not overlap the first resistance wiring 11aL in the first direction D1. Thereby, electromagnetic coupling between the first conductive wiring 11bL and the first resistance wiring 11aL is suppressed. This allows detection with higher accuracy.

A first electrical resistance R1 of the first resistance layer 11a changes depending on a state of a detection target around the first element 10A.

As shown in FIG. 1, in the sensor 110, a controller 70 may be provided. The controller 70 may be included in the sensor 110. The controller 70 may be provided separately from the sensor 110. The controller 70 is configured to supply a first electric power to the first conductive layer 11b and to detect the first electrical resistance R1. The supply of the first electric power raises the temperature of the first film portion 11F. This also raises the temperature of the first resistance layer 11a.

The heat of the first film portion 11F, for example, propagates from the first film portion 11F to its surroundings. A part of the heat propagates to the first base 51$s$ through the first gap g1. Another part of the heat propagates upward through the first film portion 11F.

For example, the heat propagation (heat dissipation) changes depending on the state of the detection target around the first element 10A. The detection target is, for example, gas. For example, the thermal conductivity of the gas around the first element 10A depends on the elements (and/or molecules) included in the gas and their concentrations. The heat dissipation property changes depending on the state of the detection target (type and concentration of gas), and as a result, the first electrical resistance R1 of the first resistance layer 11$a$ changes. By detecting the first electrical resistance R1, it is possible to detect the state of the detection target (gas and change in gas concentration).

Thus, in the embodiment, the first electrical resistance R1 changes depending on the state of the detection target when the temperature of the first film portion 11F is raised by the first electric power supplied to the first conductive layer 11$b$.

The detection target exists in the first gap g1. The first electrical resistance R1 changes depending on the state of the detection target between the first base 51$s$ and the first film portion 11F.

In such a sensor 110, it has been found that the signal (signal corresponding to the first electrical resistance R1) obtained from the first resistance layer 11$a$ tends to include noise when the first resistance wiring 11$a$L overlaps the first conductive wiring 11$b$L. For example, a large current is supplied to the first conductive layer 11$b$ and the first conductive wiring 11$b$L for raising the temperature. It is considered that noise included in the large current causes the noise in the signal obtained from the first resistance layer 11$a$.

In the embodiment, the first resistance wiring 11$a$L and the first conductive wiring 11$b$L do not overlap each other in the first direction D1. Thereby, the coupling is suppressed and the noise is suppressed. According to the embodiment, it is possible to provide a sensor capable of improving characteristics.

In the embodiments, the first film portion 11F may further include the first conductive member 11$c$. The first conductive member 11$c$ is provided between the first resistance layer 11$a$ and the first conductive layer 11$b$. By providing the first conductive member 11$c$, it becomes easy to obtain a uniform temperature distribution in the first film portion 11F. A more stable detection characteristic can be obtained.

In the embodiment, a potential of the first conductive member 11$c$ may be fixed. The potential of the first conductive member 11$c$ is, for example, fixed to a ground potential. The first conductive member 11$c$ functions, for example, as a shield. The influence of the first conductive layer 11$b$ on the first resistance layer 11$a$ can be suppressed. The noise can be suppressed more.

For example, the first conductive member 11$c$ may be electrically connected to the first base 51$s$. For example, a first base potential of the first base 51$s$ may be substantially the same as the potential of the first conductive member 11$c$. Electromagnetic influence from the outside on the first resistance layer 11$a$ can be effectively suppressed. The detection target can be detected with higher accuracy.

In the embodiment, for example, in supplying the first electric power, a first conductive layer current flowing through the first conductive layer 11$b$ and the first conductive wiring 11$b$L is large. Thereby, the first film portion 11F can be effectively heated. On the other hand, in detecting the first electrical resistance R1, a first resistance layer current flowing through the first resistance layer 11$a$ and the first resistance wiring 11$a$L is relatively small. For example, the first conductive layer current is greater than the first resistance layer current.

The noise is likely to occur when the first conductive layer current is greater than the first resistance layer current. In the embodiment, even in such a state where the noise is likely to occur, the noise can be effectively suppressed by the first resistance wiring 11$a$L and the first conductive wiring 11$b$L being not overlapping each other.

For example, the first conductive layer current is not less than 2 times the first resistance layer current. For example, the first conductive layer current may be not less than 5 times the first resistance layer current.

As shown in FIGS. 2A and 2B, in this example, the first resistance layer 11$a$ is provided between the first base 51$s$ and the first conductive layer 11$b$. Electromagnetic noise from the outside to the first resistance layer 11$a$ can be effectively suppressed by the first base 51$s$.

In the embodiments, the electrical resistance of the first conductive layer 11$b$ may be lower than the electrical resistance of the first resistance layer 11$a$. Efficient heating can be achieved by the first conductive layer 11$b$.

The first conductive layer 11$b$ may include, for example, at least one selected from the group consisting of Au, Al, Ti, TiN and Pt. The first resistance layer 11$a$ may include, for example, at least one selected from the group consisting of Au, Al, Ti, TiN and Pt. The first conductive member 11$c$ may include, for example, at least one selected from the group consisting of Au, Al, Ti, TiN and Pt. For example, a high shielding effect can be obtained by the electrical resistance of the first conductive member 11$c$ being low.

As shown in FIGS. 1 and 3A, a part of the first conductive member 11$c$ overlaps the first conductive layer 11$b$ and the first resistance layer 11$a$ in the first direction D1. Another part of the first conductive member 11$c$ does not overlap the first conductive layer 11$b$ and the first resistance layer 11$a$ in the first direction D1. For example, in a plane (X-Y plane) crossing the first direction D1, at least a part of the outer edge 11$r$ of the first conductive member 11$c$ is outside the first conductive layer 11$b$ and the first resistance layer 11$a$. For example, the area of the first conductive member 11$c$ is larger than the area of the first conductive layer 11$b$ and larger than the area of the first resistance layer 11$a$. By such a first conductive member 11$c$, the temperature of the first film portion 11F becomes more uniform.

As shown in FIG. 1, the first resistance connecting member 21$a$C extends along a second direction D2. The second direction D2 crosses the first direction D1 from the first base 51$s$ to the first fixed member 21F. As shown in FIG. 3B, a width of the first resistance connecting member 21$a$C in a third direction D3 is defined as a first resistance connecting member width w21$a$C. The third direction D3 crosses a plane including the first direction D1 and the second direction D2. As shown in FIG. 3A, a width of the first film portion 11F in the third direction D3 is defined as a first film portion width w11F. The first resistance connecting member width w21$a$C is narrower than the first film portion width w11F. Thereby, propagation of the heat of the first film portion 11F through the first resistance connecting member 21$a$C can be suppressed. The temperature of the film part can be raised with low power consumption.

As shown in FIG. 1, the first conductive connecting member 21$b$C extends along the second direction D2. As shown in FIG. 3B, a width of first conductive connecting member 21$b$C in the third direction D3 is defined as a first conductive connecting member width w21bC. The first conductive connecting member width w21bC is narrower than the first film portion width w11F. It is possible to suppress the heat of the first film portion 11F from propagating through the first conductive connecting member 21bC. A more stable temperature is obtained.

As shown in FIG. 2A, the first resistance connecting member 21aC may further include a first conductive member wiring 11cL electrically connected to the first conductive member 11c. The first conductive connecting member 21bC may include a first conductive member wiring 11cL electrically connected to the first conductive member 11c. The first conductive member wiring 11cL may be provided for at least one of the first resistance connecting member 21aC or the first conductive connecting member 21bC.

As shown in FIGS. 1, 2A and 2B, the first element 10A may further include a first other fixed member 21 FA fixed to the first base 51s, a first other resistance connecting member 21aCA supported by the first other fixed member 21 FA, and a first other conductive connecting member 21bCA supported by the first other fixed member 21FA. The first other resistance connecting member 21aCA and the first other conductive connecting member 21bCA support the first film portion 11F.

As shown in FIGS. 2B and 3C, the first other resistance connecting member 21aCA includes a first other resistance wiring 11aLA electrically connected to the first resistance layer 11a. As shown in FIGS. 2A and 3C, the first other conductive connecting member 21bCA includes a first other conductive wiring 11bLA electrically connected to the first conductive layer 11b.

For example, in the first direction D1, the first other resistance wiring 11aLA does not overlap the first other conductive wiring 11bLA. Electromagnetic coupling between the first other resistance wiring 11aLA and the first other conductive wiring 11bLA is suppressed. Thereby, the noise can be suppressed more.

For example, the controller 70 is configured to supply the first electric power to the first conductive layer 11b through the first conductive wiring 11bL and the first other conductive wiring 11bLA. The controller 70 is configured to acquire a value corresponding to the first electrical resistance R1 via the first resistance wiring 11aL and the first other resistance wiring 11aLA.

As shown in FIG. 3A, an insulating member 111 may be provided around the first resistance layer 11a. The insulating member 111 may be provided for the first resistance connecting member 21aC, the first other resistance connecting member 21aCA, the first conductive connecting member 21bC and the first other conductive connecting member 21bCA.

In the embodiment, as shown in FIG. 1, the first film portion 11F may be provided between the first resistance connecting member 21aC and the first other resistance connecting member 21aCA. For example, the first film portion 11F may be provided between the first conductive connecting member 21bC and the first other conductive connecting member 21bCA.

In the example of FIG. 1, the direction from the first resistance connecting member 21aC to the first other resistance connecting member 21aCA is along the direction from the first conductive connecting member 21bC to the first other conductive connecting member 21bCA.

In the embodiment, the direction from the first resistance connecting member 21aC to the first other resistance connecting member 21aCA may cross the direction from the first conductive connecting member 21bC to the first other conductive connecting member 21bCA.

In the embodiment, the direction from the first film portion 11F to the first resistance connecting member 21aC may cross the direction from the first film portion 11F to the first other resistance connecting member 21aCA. The direction from the first film portion 11F to the first conductive connecting member 21bC may cross the direction from the first film portion 11F to the first other conductive connecting member 21bCA.

Figure 4A:
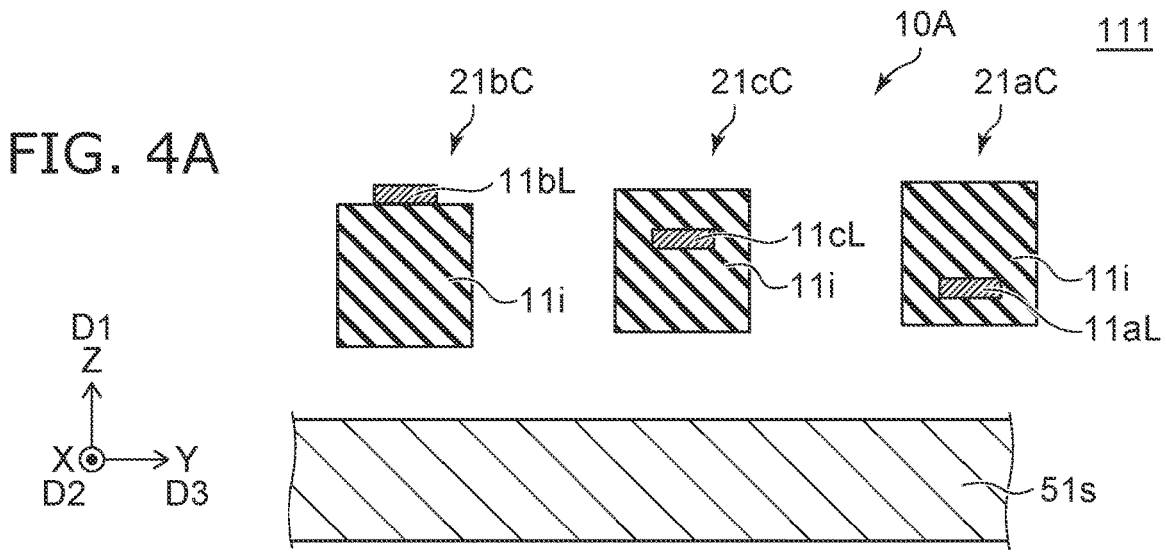
FIGS. 4A and 4B are schematic cross-sectional views illustrating a part of a sensor according to the first embodiment.
Figure 4B:
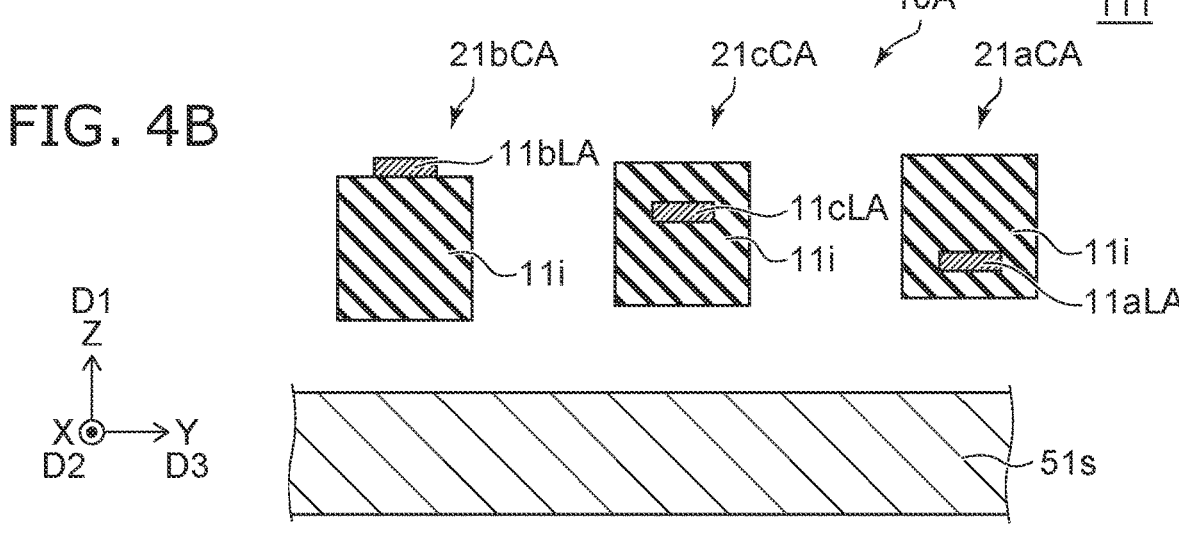

FIGS. 4A and 4B are schematic cross-sectional views illustrating a part of a sensor according to the first embodiment.

FIG. 4A is a cross-sectional view corresponding to the line B3-B4 in FIG. 1. FIG. 4B is a cross-sectional view corresponding to the line B5-B6 in FIG. 1. As shown in FIG. 4A, in a sensor 111 according to the embodiment, the first element 10A includes a first conductive member connecting member 21cC and a first other conductive member connecting member 21cCA. Except for this, the configuration of the sensor 111 may be the same as the configuration of the sensor 110, for example.

In the sensor 111, the first conductive member connecting member 21cC is supported by the first fixed member 21F. The first conductive member connecting member 21cC includes a first conductive member wiring 11cL electrically connected to the first conductive member 11c. The first other conductive member connecting member 21cCA is supported by the first other fixed member 21FA (see FIG. 1). The first other conductive member connecting member 21cCA includes a first other conductive member wiring 11cLA electrically connected to the first conductive member 11c.

The wirings respectively connected to the first resistance layer 11a, the first conductive layer 11b, and the first conductive member 11c may be provided in different connection portions. The noise can also be suppressed in the sensor 111.

Figure 5:
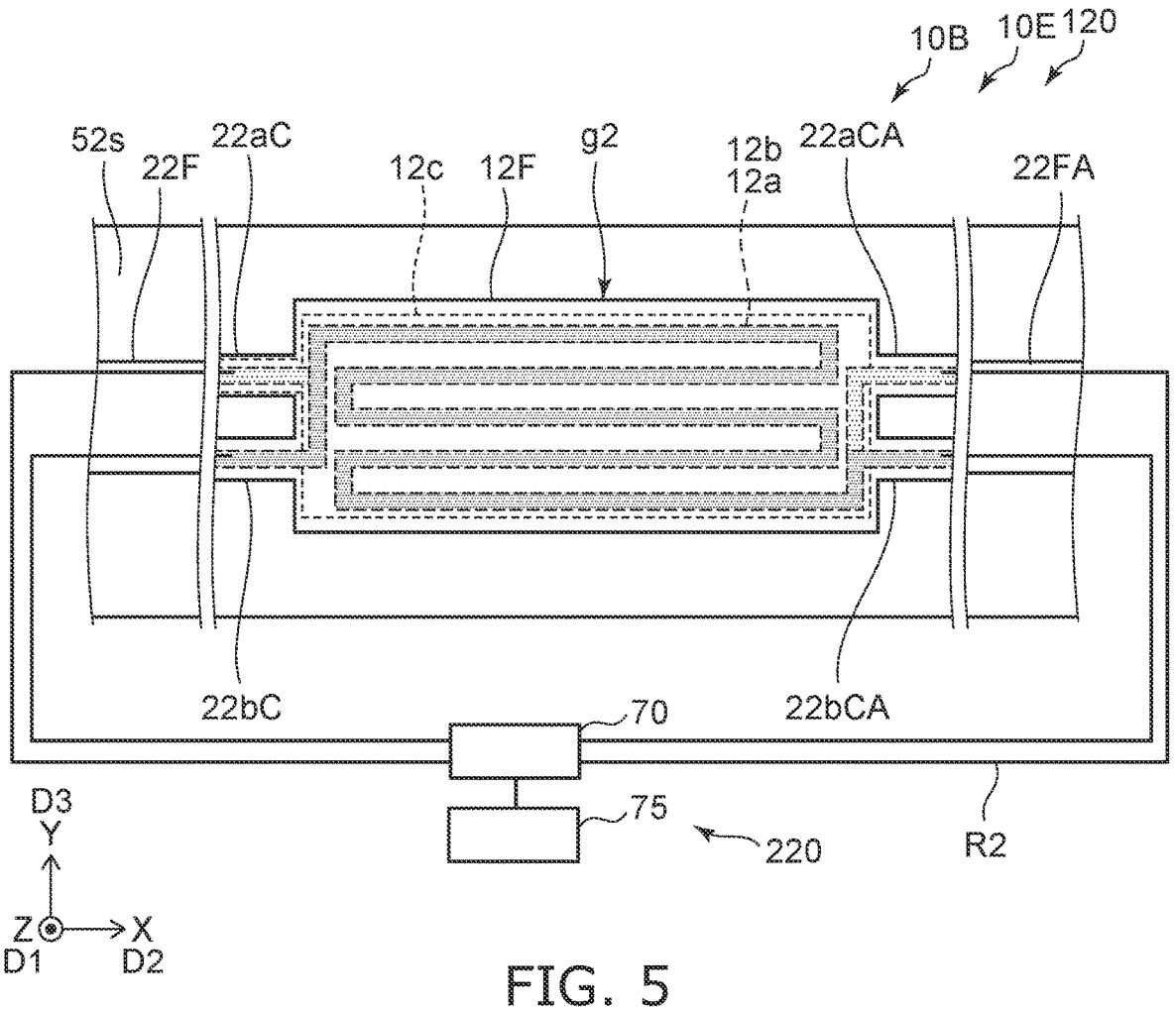
FIG. 5 is a schematic plan view illustrating a part of a sensor according to the first embodiment.

FIG. 5 is a schematic plan view illustrating a part of a sensor according to the first embodiment.

As shown in FIG. 5, in a sensor 120 according to the embodiment, the element portion 10 E includes a second base 52s and a second element 10B in addition to the first base 51s and the first element 10A (omitted in FIG. 5) described with respect to FIG. 1. In the sensor 120, the configuration of the first base 51s and the first element 10A may be similar to those in the sensor 110.

In the sensor 120, the second element 10B includes a second fixed member 22F fixed to the second base 52s, a second resistance connecting member 22aC supported by the second fixed member 22F, and a second film portion 12F supported by the second resistance connecting member 22aC. A second gap g2 is provided between the second base 52s and the second film portion 12F. The second base 52s may be continuous with the first base 51s. The boundary between the second base 52s and the first base 51s may be clear or unclear.

The second film portion 12F includes a second resistance layer 12a. The controller 70 is configured to output a value corresponding to a difference between the second electrical resistance R2 of the second resistance layer 12a and the first electrical resistance R1 (see FIG. 1). The controller 70 includes, for example, a differential amplifier.

The second element 10B is, for example, a reference element. For example, influences such as fluctuations in ambient temperature are suppressed. Higher accuracy detection is possible.

In this example, the second film portion 12F includes a second conductive layer 12b. Power need not be supplied to the second conductive layer 12b. The second conductive layer 12b may not be used for the detection. The second conductive layer 12b functions, for example, as a dummy conductive layer.

In this example, the second film portion 12F includes a second conductive member 12c. The second conductive member 12c overlaps, for example, the second resistance layer 12a and the second conductive layer 12b. For example, the potential of the second conductive member 12c may be fixed. The temperature of the second film portion 12F is made uniform by the second conductive member 12c.

In the embodiment, the second conductive layer 12b and the second conductive member 12c may be omitted. Alternatively, the configuration of the second element 10B may be substantially the same as the configuration of the first element 10A. The first element 10A and the second element 10B have substantially the same heat capacity and the like, which enables detection with higher accuracy.

In the sensor 120, the second element 10 B may include a second conductive connecting member 22bC supported by the second fixed member 22F. The second conductive connecting member 22bC supports the second film portion 12F. The second element 10B may include a second other fixed member 22FA fixed to the second base 52s, a second other resistance connecting member 22aCA supported by the second other fixed member 22FA, and a second other conductive connecting member 22bCA supported by the second other fixed member 22FA. The second other resistance connecting member 22aCA and the second other conductive connecting member 22bCA support the second film portion 12F.

Second Embodiment

The second embodiment relates to a sensor system. As shown in FIGS. 1 and 5, sensor systems 210 and 220 according to embodiments include the sensor according to embodiments (sensors 110 and 120) and a communicator 75. The communicator 75 is configured to transmit a signal corresponding to the change in the first electrical resistance R1. According to the embodiment, low noise sensor signals can be obtained from a remote location.

The communicator 75 is configured to supply signals to the outside, for example, by at least one of wired method or wireless method. The communicator 75 may be configured to acquire a control signal from the outside. The controller 70 may be controlled by the control signal from the outside.

The embodiments may include the following configurations (for example, technical proposals).

Configuration 1

A sensor, comprising:
an element portion including a first base and a first element,
the first element including
   a first fixed member fixed to the first base,
   a first resistance connecting member supported by the first fixed member,
   a first conductive connecting member supported by the first fixed member, and
   a first film portion supported by the first resistance connecting member and the first conductive connecting member, a first gap being provided between the first base and the first film portion,
   the first film portion including a first resistance layer and a first conductive layer,
   the first resistance connecting member including a first resistance wiring electrically connected to the first resistance layer, and
   the first conductive connecting member including a first conductive wiring electrically connected to the first conductive layer.

Configuration 2

The sensor according to Configuration 1, wherein
the first resistance connecting member does not include the first conductive wiring, and
the first conductive connecting member does not include the first resistance wiring.

Configuration 3

The sensor according to Configuration 1 or 2, wherein
the first film portion further includes a first conductive member, and
the first conductive member is provided between the first resistance layer and the first conductive layer.

Configuration 4

The sensor according to Configuration 1 or 2, wherein
the first film portion further includes a first conductive member,
the first conductive member is provided between the first resistance layer and the first conductive layer, and
a potential of the first conductive member is fixed.

Configuration 5

The sensor according to Configuration 3, wherein
a first base potential of the first base is substantially the same as a potential of the first conductive member.

Configuration 6

The sensor according to any one of Configurations 3-5, wherein
   the first element further includes a first conductive member connecting member supported by the first fixed member, and
   the first conductive member connecting member includes a first conductive member wiring electrically connected to the first conductive member.

Configuration 7

The sensor according to any one of Configurations 3-5, wherein
   the first resistance connecting member further includes a first conductive member wiring electrically connected to the first conductive member.

Configuration 8

The sensor according to any one of Configurations 3-5, wherein the first conductive connecting member includes a first conductive member wiring electrically connected to the first conductive member.

Configuration 9

The sensor according to any one of Configurations 1-8, wherein a first electrical resistance of the first resistance layer changes according to a state of a detection target around the first element.

Configuration 10

The sensor according to Configuration 9, wherein in a state in which a temperature of the first film portion is raised by a first electric power supplied to the first conductive layer, the first electrical resistance changes depending on the state of the detection target.

Configuration 11

The sensor according to Configuration 9 or 10, wherein the first electrical resistance changes according to the state of the detection target between the first base and the first film portion.

Configuration 12

The sensor according to any one of Configurations 1-11, wherein the first resistance layer is provided between the first base and the first conductive layer.

Configuration 13

The sensor according to any one of Configurations 1-12, wherein the first resistance connecting member extends in a second direction crossing a first direction from the first base to the first fixed member, a first resistance connecting member width of the first resistance connecting member in a third direction crossing a plane including the first direction and the second direction is narrower than a first film portion width of the first film portion in the third direction.

Configuration 14

The sensor according to Configuration 13, wherein the first conductive connecting member extends along the second direction, and a first conductive connection member width of the first conductive connecting member in the third direction is narrower than the first film portion width.

Configuration 15

The sensor according to Configuration 10, wherein the first element include a first other fixed member fixed to the first base, a first other resistance connecting member supported by the first other fixed member, and a first other conductive connecting member supported by the first other fixed member, the first other resistance connecting member and the first other conductive connecting member support the first film portion, the first resistance connecting member includes a first resistance wiring electrically connected to the first resistance layer, and the first other conductive connecting member includes a first other conductive wiring electrically connected to the first conductive layer.

Configuration 16

The sensor according to Configuration 15, further comprising:

a controller, the controller being configured to supply the first electric power to the first conductive layer, and the controller being configured to output a signal corresponding to the first electrical resistance.

Configuration 17

The sensor according to Configuration 16, wherein the controller is configured to supply the first electric power to the first conductive layer through the first conductive wiring and the first other conductive wiring, and the controller is configured to acquire a value corresponding to the first electrical resistance via the first resistance wiring and the first other resistance wiring.

Configuration 18

The sensor according to Configuration 16 or 17, wherein a first conductive layer current flowing in the first conductive layer in supplying the first electric power is greater than a first resistance layer current flowing in the first resistance layer in sensing the first electrical resistance.

Configuration 19

The sensor according to any one of Configurations 16-18, wherein the element section further includes a second base and a second element, the second element includes a second fixed member fixed to the second base, a second resistance connecting member supported by the second fixed member, and a second film portion supported by the second resistance connecting member, a second gap is provided between the second base and the second film portion, the second film portion includes a second resistance layer, and the controller is configured output a value corresponding to a difference between a second electrical resistance of the second resistance layer and the first electrical resistance.

Configuration 20

A sensor system, comprising:

the sensor according to any one of Configurations 9-19; and a communicator configured to transmit a signal corresponding to a change in the first electrical resistance.

According to the embodiments, a sensor and a sensor system capable of improving accuracy can be provided.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors and sensor systems such as, bases, element sections, fixed members, connecting members, film portions, controllers, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors and all sensor systems practicable by an appropriate design modification by one skilled in the art based on the sensors and the sensor systems described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:

an element portion including a first base and a first element, the first element including a first fixed member fixed to the first base, a first resistance connecting member supported by the first fixed member, a first conductive connecting member supported by the first fixed member, and a first film portion supported by the first resistance connecting member and the first conductive connecting member, a first gap being provided between the first base and the first film portion, the first film portion including a first resistance layer and a first conductive layer, the first resistance connecting member including a first resistance wiring electrically connected to the first resistance layer, and the first conductive connecting member including a first conductive wiring electrically connected to the first conductive layer, wherein the first film portion further includes a first conductive member, and the first conductive member is provided between the first resistance layer and the first conductive layer.

2. The sensor according to claim 1, wherein the first resistance connecting member does not include the first conductive wiring, and the first conductive connecting member does not include the first resistance wiring.

3. The sensor according to claim 1, wherein a potential of the first conductive member is fixed.

4. The sensor according to claim 1, wherein a first base potential of the first base is substantially the same as a potential of the first conductive member.

5. The sensor according to claim 1, wherein the first element further includes a first conductive member connecting member supported by the first fixed member, and the first conductive member connecting member includes a first conductive member wiring electrically connected to the first conductive member.

6. The sensor according to claim 1, wherein the first resistance connecting member further includes a first conductive member wiring electrically connected to the first conductive member.

7. The sensor according to claim 1, wherein the first conductive connecting member includes a first conductive member wiring electrically connected to the first conductive member.

8. The sensor according to claim 1, wherein a first electrical resistance of the first resistance layer changes according to a state of a detection target around the first element.

9. The sensor according to claim 8, wherein in a state in which a temperature of the first film portion is raised by a first electric power supplied to the first conductive layer, the first electrical resistance changes depending on the state of the detection target.

10. The sensor according to claim 9, wherein the first element include a first other fixed member fixed to the first base, a first other resistance connecting member supported by the first other fixed member, and a first other conductive connecting member supported by the first other fixed member, the first other resistance connecting member and the first other conductive connecting member support the first film portion, the first other resistance connecting member includes a first other resistance wiring electrically connected to the first resistance layer, and the first other conductive connecting member includes a first other conductive wiring electrically connected to the first conductive layer.

11. The sensor according to claim 10, further comprising:

a controller, the controller being configured to supply the first electric power to the first conductive layer, and the controller being configured to output a signal corresponding to the first electrical resistance.

12. The sensor according to claim 11, wherein the controller is configured to supply the first electric power to the first conductive layer through the first conductive wiring and the first other conductive wiring, and the controller is configured to acquire a value corresponding to the first electrical resistance via the first resistance wiring and the first other resistance wiring.

13. The sensor according to claim 11, wherein a first conductive layer current flowing in the first conductive layer in supplying the first electric power is greater than a first resistance layer current flowing in the first resistance layer in sensing the first electrical resistance.

14. The sensor according to claim 11, wherein the element portion further includes a second base and a second element, the second element includes a second fixed member fixed to the second base, a second resistance connecting member supported by the second fixed member, and a second film portion supported by the second resistance connecting member, a second gap is provided between the second base and the second film portion, the second film portion includes a second resistance layer, and the controller is configured output a value corresponding to a difference between a second electrical resistance of the second resistance layer and the first electrical resistance.

15. The sensor according to claim 8, wherein the first electrical resistance changes according to the state of the detection target between the first base and the first film portion.

16. A sensor system, comprising:

the sensor according to claim 8; and a communicator configured to transmit a signal corresponding to a change in the first electrical resistance.

17. The sensor according to claim 1, wherein the first resistance layer is provided between the first base and the first conductive layer.

18. The sensor according to claim 1, wherein the first resistance connecting member extends in a second direction crossing a first direction from the first base to the first fixed member, a first resistance connecting member width of the first resistance connecting member in a third direction crossing a plane including the first direction and the second direction is narrower than a first film portion width of the first film portion in the third direction.

19. The sensor according to claim 18, wherein the first conductive connecting member extends along the second direction, and a first conductive connection member width of the first conductive connecting member in the third direction is narrower than the first film portion width.

20. A sensor, comprising:

an element portion including a first base and a first element, the first element including a first fixed member fixed to the first base, a first resistance connecting member supported by the first fixed member, a first conductive connecting member supported by the first fixed member, and a first film portion supported by the first resistance connecting member and the first conductive connecting member, a first gap being provided between the first base and the first film portion, the first film portion including a first resistance layer and a first conductive layer, the first resistance connecting member including a first resistance wiring electrically connected to the first resistance layer, and the first conductive connecting member including a first conductive wiring electrically connected to the first conductive layer, wherein the first element include a first other fixed member fixed to the first base, a first other resistance connecting member supported by the first other fixed member, and a first other conductive connecting member supported by the first other fixed member, the first other resistance connecting member and the first other conductive connecting member support the first film portion, the first other resistance connecting member includes a first other resistance wiring electrically connected to the first resistance layer, and the first other conductive connecting member includes a first other conductive wiring electrically connected to the first conductive layer.

\* \* \* \* \*